United States Patent
Wong (10) Patent No.: US 7,385,690 B2
(45) Date of Patent: Jun. 10, 2008

(54) INSPECTING SYSTEM FOR COLOR FILTERS

(75) Inventor: Ren-Sue Wong, Sunnyvale, CA (US)

(73) Assignee: ICF Technology Limited., Santa Clara, CA (US)

( * ) Notice: Subject to any disclaimer, the term of this patent is extended or adjusted under 35 U.S.C. 154(b) by 235 days.

(21) Appl. No.: 11/410,237

(22) Filed: Apr. 24, 2006

(65) Prior Publication Data

US 2007/0247619 A1    Oct. 25, 2007

(51) Int. Cl.
*G01N 21/00* (2006.01)

(52) U.S. Cl. .................................. 356/239.2

(58) Field of Classification Search .. 356/237.1–237.5, 356/239.1–239.3; 349/149, 192; 250/559.45; 430/7
See application file for complete search history.

(56) References Cited

U.S. PATENT DOCUMENTS 5,400,135 A * 3/1995 Maeda .................... 356/239.1
6,221,544 B1   4/2001 Hayashi et al.
6,842,240 B2 * 1/2005 Ueta ........................ 356/239.2
2001/0030728 A1* 10/2001 Takasugi et al. ............ 349/149

* cited by examiner

*Primary Examiner*—Hoa Q Pham
(74) *Attorney, Agent, or Firm*—Jeffrey T. Knapp (57) ABSTRACT

An inspecting system (100) includes a stage (10), a white light source (20), a CCD camera (40), a laser diode assembly (60), at least one beam splitter (36, 34), a photo diode (50), and an oscilloscope (52). The white light source emits a white light (22) to illuminate a color filter (200). The CCD camera photographs the color filter and is linked with an image processing and displaying device (42). The laser diode assembly emits a laser light (62). The at least one beam splitter is arranged in a path of the laser light and transmits the laser light to the color filter. The photo diode receives the laser light reflected by the color filter and generates an electronic signal. The oscilloscope is connected with the photo diode and displays the electronic signal. The inspecting system facilitates the convenient and accurate inspection/evaluation of color filters.

19 Claims, 15 Drawing Sheets

Figure 1:
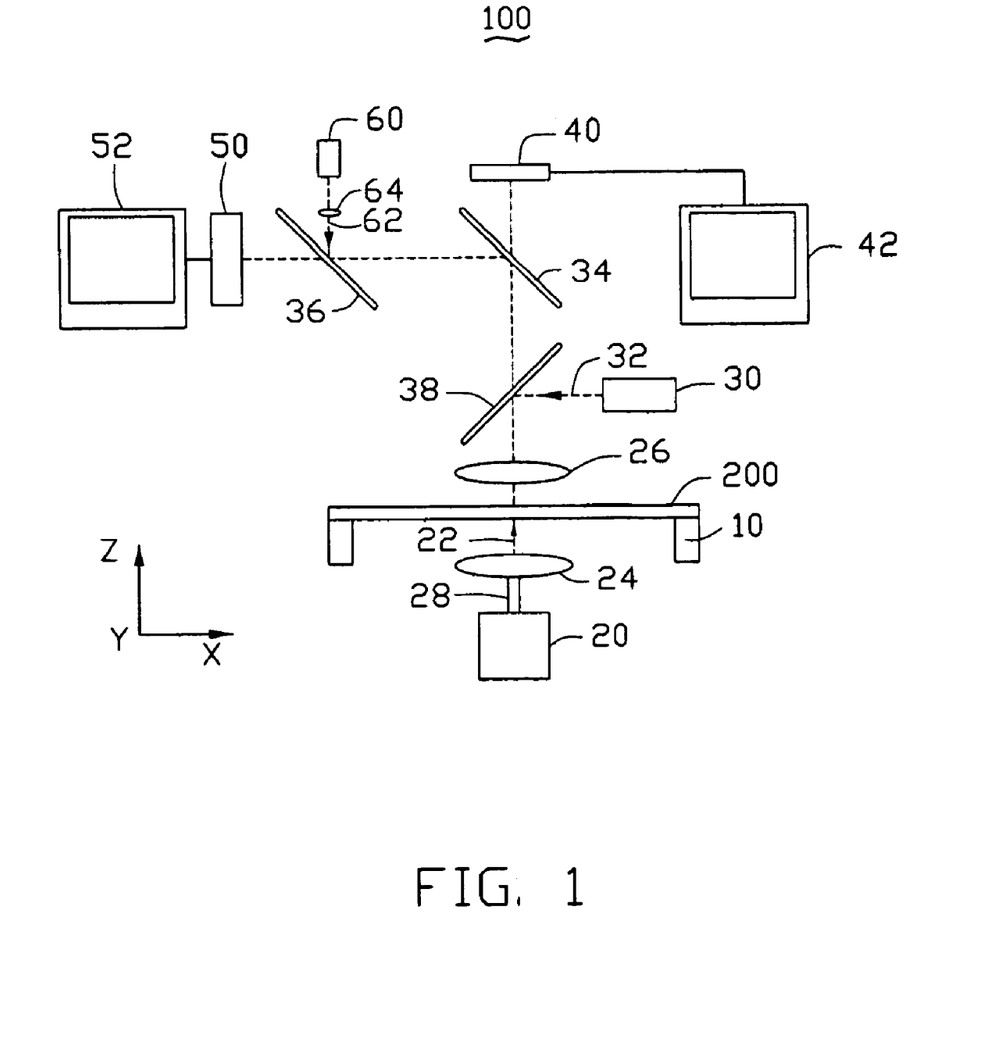
FIG. 1 is a schematic, plan view of an inspecting system, in accordance with a first embodiment.

FIG. 9 ered between the black matrix and the glass substrate. In order to focus the illuminating light 22 on a desirable spot of the color filter 200, a lens 24 can be mounted between the light source 20 and the color filter 200. Further, an optical fiber 28 can be used for guiding the light 22 emitted from the light source 20 to the lens 24, so that any of various mounting places of the light source 20 can be chosen.
INSPECTING SYSTEM FOR COLOR FILTERS

BACKGROUND OF THE INVENTION

1. Field of the Invention

The present invention relates to an inspecting system for inspecting color filters.

2. Discussion of the Related Art

A liquid crystal display (LCD) utilizes a color filter to display images and graphs. The color filter is generally constructed by arranging colored portions colored in red (R), green (G), and blue (B), as three primary colors of light on a transparent substrate. A dyeing method, a pigment dispersing method, and/or an electrodepositing method, etc. are typically used as manufacturing methods of the color filter. Recently, an ink jet system, simple in process and economically advantageous, has been used.

In order to ensure quality, a half-finished color filter and a finished color filter must be inspected in a manufacturing process. In a typical defect inspection of a color filter, an inspection person normally visually checks the color filter. Since this defect inspection method depends on the sensory organs and cognitive abilities of people, the defect inspection result varies depending on the abilities of the inspection personnel and/or on the error rates of such personnel, making it is difficult to attain a stable defect inspection.

What is needed, therefore, is an inspecting system that can aid persons to conveniently and accurately inspect color filters.

SUMMARY OF THE INVENTION

An inspecting system for color filters according to one preferred embodiment includes a stage, a white light source, a CCD camera, a laser diode assembly, at least one beam splitter, a photo diode, and a first signal processing and displaying device. The stage supports the color filter. The white light source emits a white light to illuminate the color filter from a first side of the color filter. The CCD camera is used for photographing the color filter from a second side opposite to the first side of the color filter. This CCD camera further connects with an image processing and displaying device. The laser diode assembly is configured to emit a laser light. The at least one beam splitter is arranged in a path of the laser light and is used for transmitting the laser light to the color filter. The photo diode receives the laser light reflected by the color filter and generates an electronic signal. The first signal processing and displaying device connects with the photo diode. The inspecting system can aid in the convenient and accurate inspection/examination of color filters.

Other advantages and novel features will become more apparent from the following detailed description of present inspecting system, when taken in conjunction with the accompanying drawings.

BRIEF DESCRIPTION OF THE DRAWINGS

Many aspects of the present inspecting system can be better understood with reference to the following drawings. The components in the drawings are not necessarily to scale, the emphasis instead being placed upon clearly illustrating the principles of the present inspecting system. Moreover, in the drawings, like reference numerals designate corresponding parts throughout the several views.

DETAILED DESCRIPTION OF PREFERRED EMBODIMENTS

Reference will now be made to the drawings to describe preferred embodiment of the present inspecting system, in detail.

Referring to FIG. 1, an inspecting system 100 for inspecting color filters, in accordance with a first embodiment, is shown. The inspecting system 100 includes a stage 10, a CCD (charge coupled device) camera 40, a photo diode 50, and three light sources 20, 30, 60. The CCD camera 40 connects with an image processing and displaying device 42. The photo diode 50 operatively links with a signal processing and displaying device 52. Three beam splitters 38, 34 and 36 are arranged in light paths of the light sources 20, 30, 60.

Specifically, the light source 20 can, advantageously, be a white light source. The light source 20 is used for emitting an illuminating light 22 to illuminate a color filter 200 located on the stage 10 from a backside thereof. The color filter 200 can be a half-finished color filter, only including a glass substrate and a black matrix formed thereon, or it can be a finished color filter including a glass substrate, a black matrix, and R-G-B colored portions form The light source 30 can be an LED (light emitting diode) or another light source. The light source 30 is used for emitting an illuminating light 32 to illuminate the color filter 200 from an upper side thereof. A lens 26 can be adopted to focus the illuminating light 32 emitted from the light source 30 on the color filter 200. The light source 60 is advantageously a laser diode assembly having a lens 64. The light source 60 is configured for emitting a laser light 62, and the lens 64 is used for focusing the laser light 62 on a spot of the color filter 200. Preferably, the focused spot of the laser light 62 has a size smaller than that of a black matrix of the color filter 200.

The beam splitters 38 and 34 are arranged between the CCD camera 40 and the lens 26. The beam splitters 36 and 34 are configured for reflecting the laser light 62 emitted from the light source 60 to the color filter 200 through the beam splitter 38 and for then transmitting the laser light 62 reflected back by the color filter 200 through the beam splitter 38. Though the lights 22, 32, 62 are shown in FIG. 1, the light sources 20, 30, 60 actually do not work at the same time. The actual working states of the light sources 20, 30, 60 will be detailed described in following paragraphs of operation of the inspecting system 100.

The stage 10 is, beneficially, an XY control stage with an exact coordinate system. The stage 10 is configured for supporting the color filter 200 thereon, and the coordinate system can be used to locate the color filter 200 during an inspecting process. The image processing and displaying device 42 includes a monitor adapted/designed for displaying an image of the color filter 200 photographed by the CCD camera 40. In the preferred embodiment, the signal processing and displaying device 52 usefully is an oscilloscope capable of displaying an electronic signal generated by the photo diode 50.

The inspecting system 100 can be used for inspecting the half-finished color filter, the finished color filter, and so on. Following are detailed descriptions of situations employing the inspecting system 100.

Figure 2A:
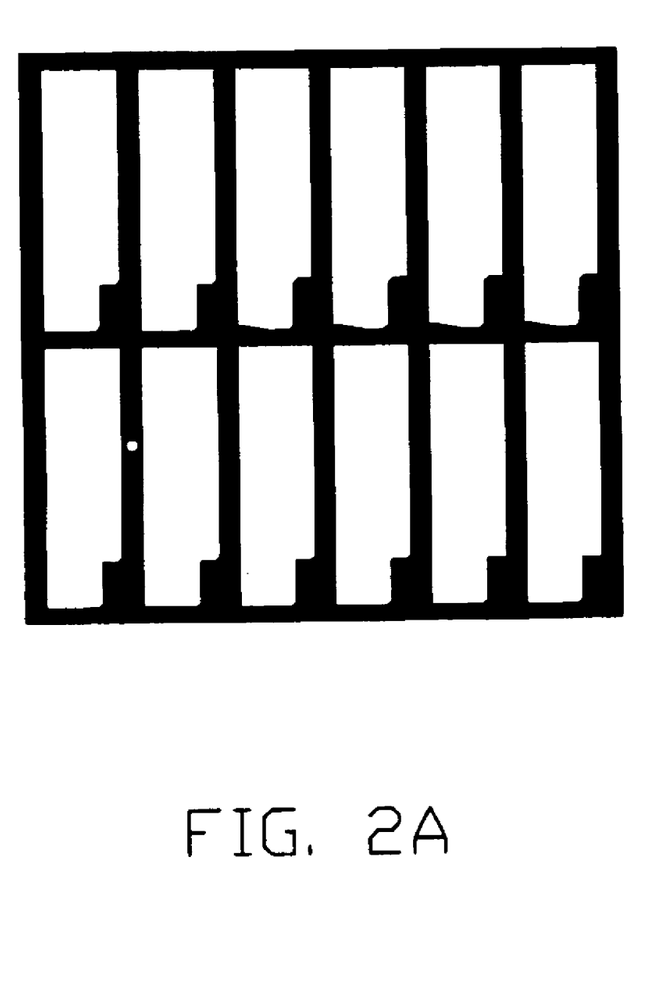
FIGS. 2A and 2B are an image and a graph displayed by the inspecting system of FIG. 1 in a first inspecting method.
Figure 2B:
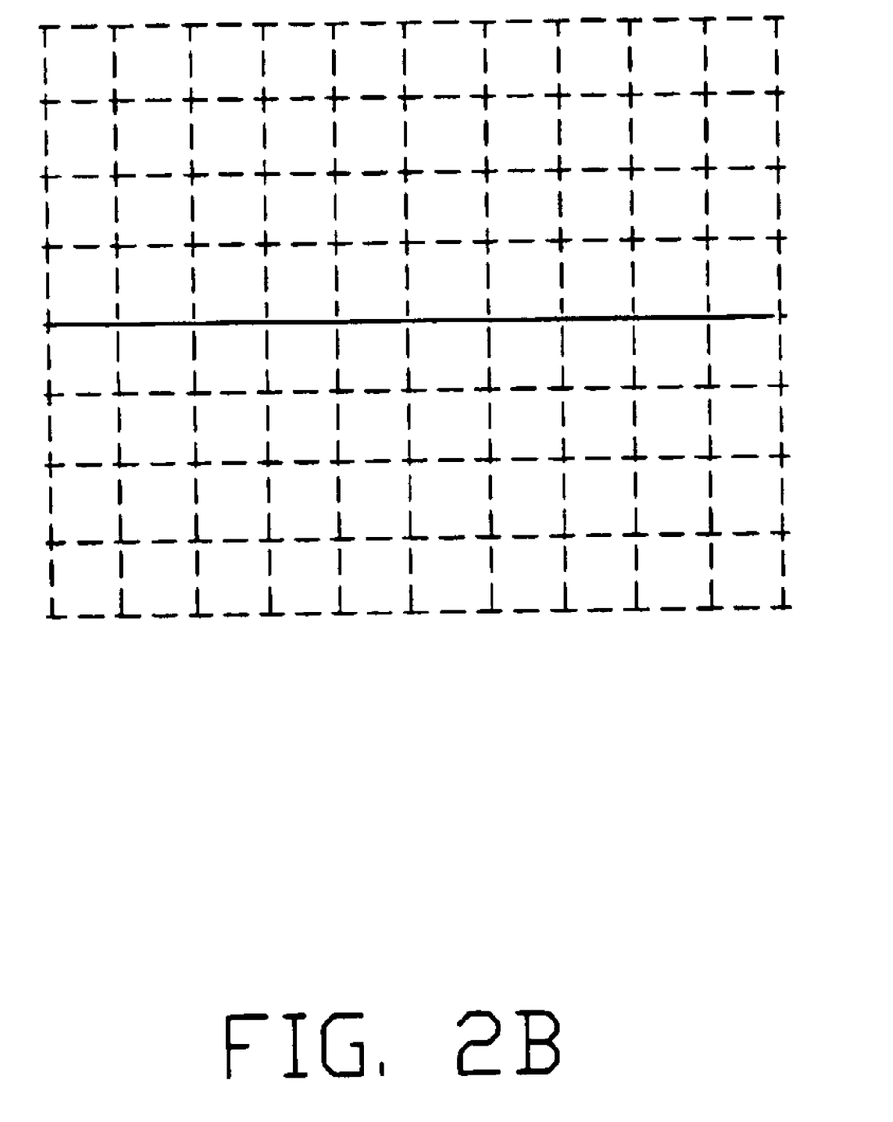

Referring to FIGS. 1 and 2, in a first method for inspecting the half-finished color filter 200, the stage 10 is kept immobile and only the light sources 30, 60 are turned on. Under this condition, the light source 30 emits the illuminating light 32, and the light source 60 emits the laser light 62. The illuminating light 32 incidences upon the beam splitter 38 and is reflected to the lens 26 by the beam splitter 38. The lens 26 focuses the illuminating light 32 on a spot of the half-finished color filter 200. Thus, the CCD camera 40 can photograph the illuminated portion of the color filter 200, and a photographed image of the illuminated portion is displayed on the monitor of the image processing and displaying device 42 (referring to FIG. 2A). Because the image is enlarged, an inspection person can conveniently inspect the quality of the black matrix of the half-finished color filter 200.

At the same time, the laser light 62 is focused by the lens 64, then incidences upon the beam splitter 36, and is ultimately reflected to the beam splitter 34 by the beam splitter 36. The beam splitter 34 reflects the laser light 62 to the beam splitter 32, and the beam splitter 32 transmits the laser light 62 to the lens 26. The lens 26 further focuses the laser light 62 on a spot of the half-finished color filter 200. As mentioned above, the spot size of the focused laser light 62 is generally smaller than that of the black matrix of the color filter 200, so the laser light 62 can be reflected back to the beam splitter 36 by the black matrix along a reverse path. Then, the laser light 62 passes through the beam splitter 36 and incidences upon the photo diode 50. The photo diode 50 receives the light signal of the laser light 62 and generates a corresponding electronic signal. The oscilloscope 52 displays the electronic signal and aids the inspection of the quality of the black matrix of the half-finished color filter 200 in another manner (referring to FIG. 2B). Because the stage 10 and the color filter 200 are motionless, the signal displayed on the oscilloscope 52 is a level line.

Figure 3A:
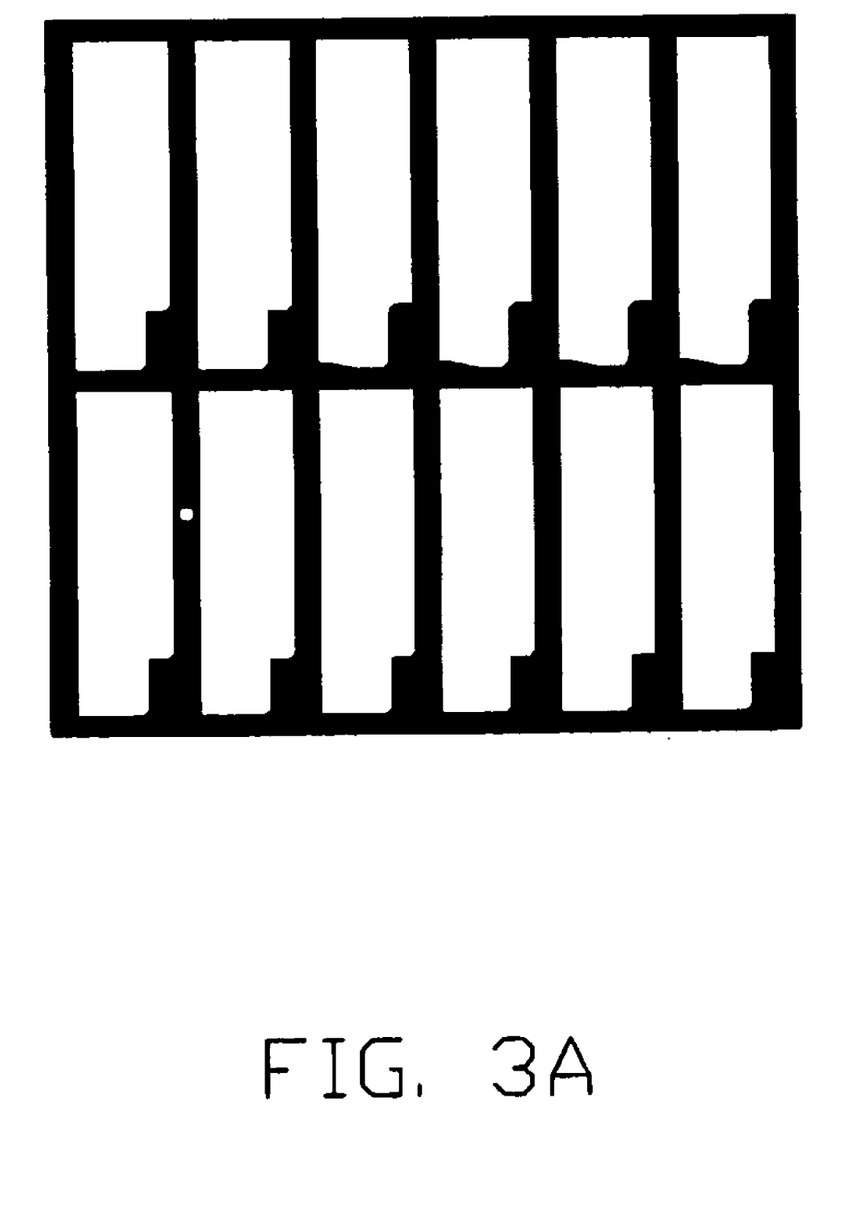
FIGS. 3A and 3B are an image and a graph displayed by the inspecting system of FIG. 1 in a second inspecting method.
Figure 3B:
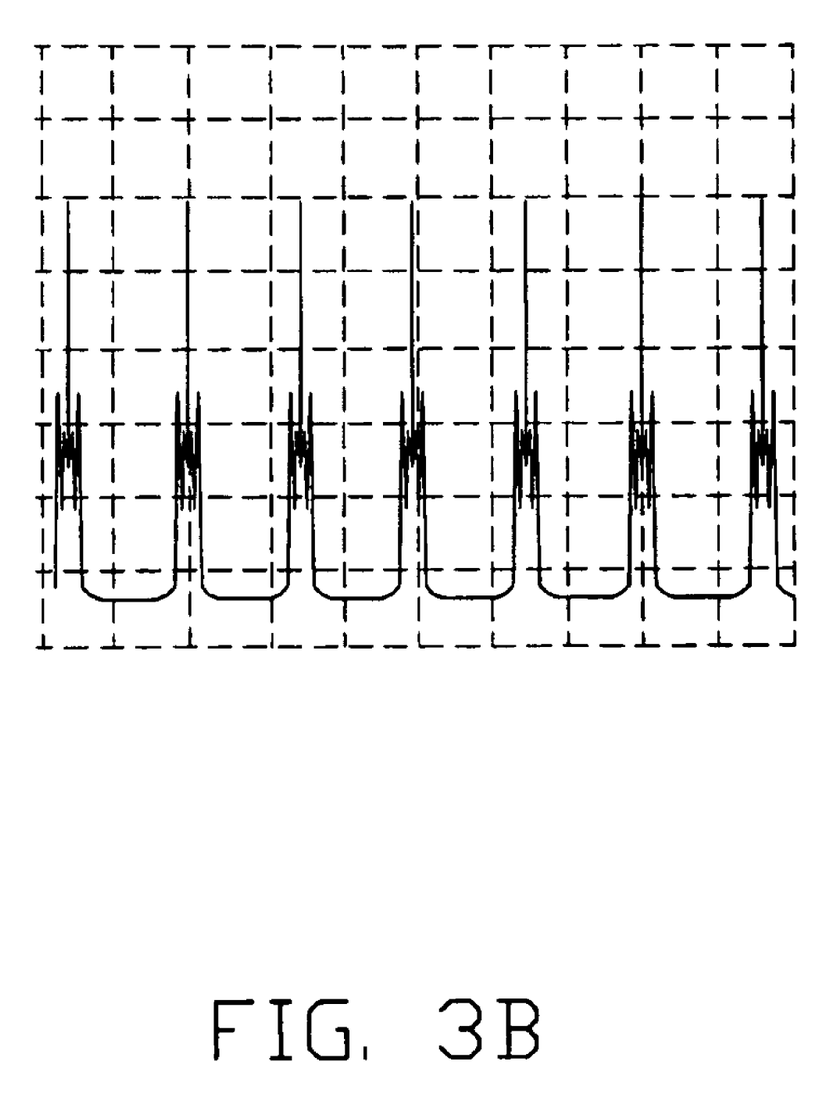

Referring to FIGS. 1 and 3, in a second method for inspecting the half-finished color filter 200, the stage 10 is moved along a X direction, and only the light source 60 is turned on. Under this condition, the laser light 62 firstly is focused on a spot of the half-finished color filter 200 along a path similar to that of the first method, then is reflected to the beam splitter 36 by the black matrix or the glass substrate along a reverse path, as mentioned above. The reflected laser light 62 passes through the beam splitter 36 and incidences upon the photo diode 50. The photo diode 50 receives the light signal of the laser light 62 and generates a corresponding electronic signal. The oscilloscope 52 displays the electronic signal and aids the inspection of the quality of the black matrix of the half-finished color filter 200 (referring to FIG. 3B). The CCD camera 40 still can photograph a portion of the color filter 200, and a photographed image of the portion is displayed on the monitor of the image processing and displaying device 42 (referring to FIG. 3A). Because the image is enlarged, the inspection person can conveniently evaluate the quality of the black matrix of the color filter 200. Because the stage 10 and the color filter 200 are moving, the signal displayed on the oscilloscope 52 is a curved line. The peak signal on the oscilloscope indicates the position of the black matrix.

Figure 4A:
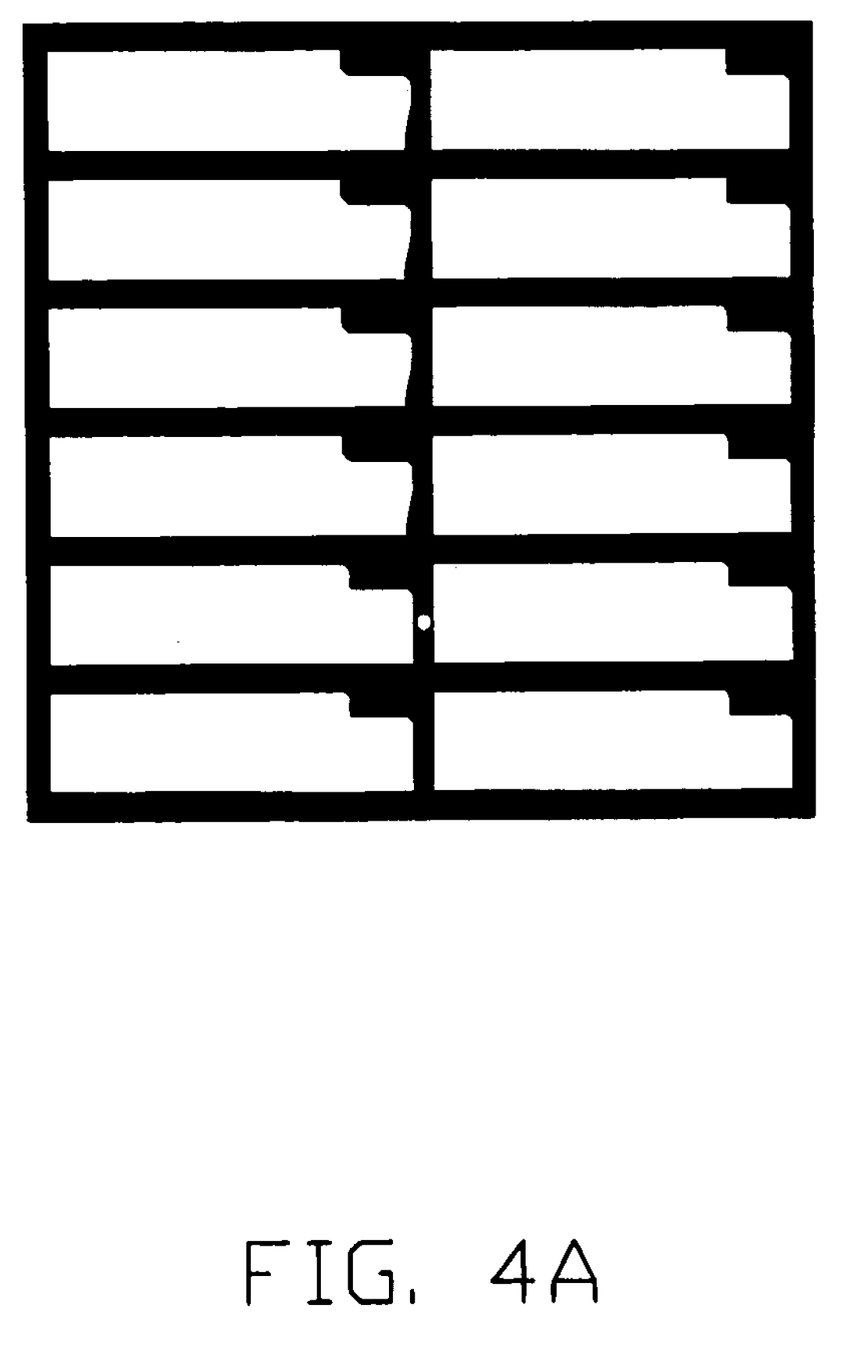
FIGS. 4A and 4B are an image and a graph displayed by the inspecting system of FIG. 1 in a third inspecting method.
Figure 4B:
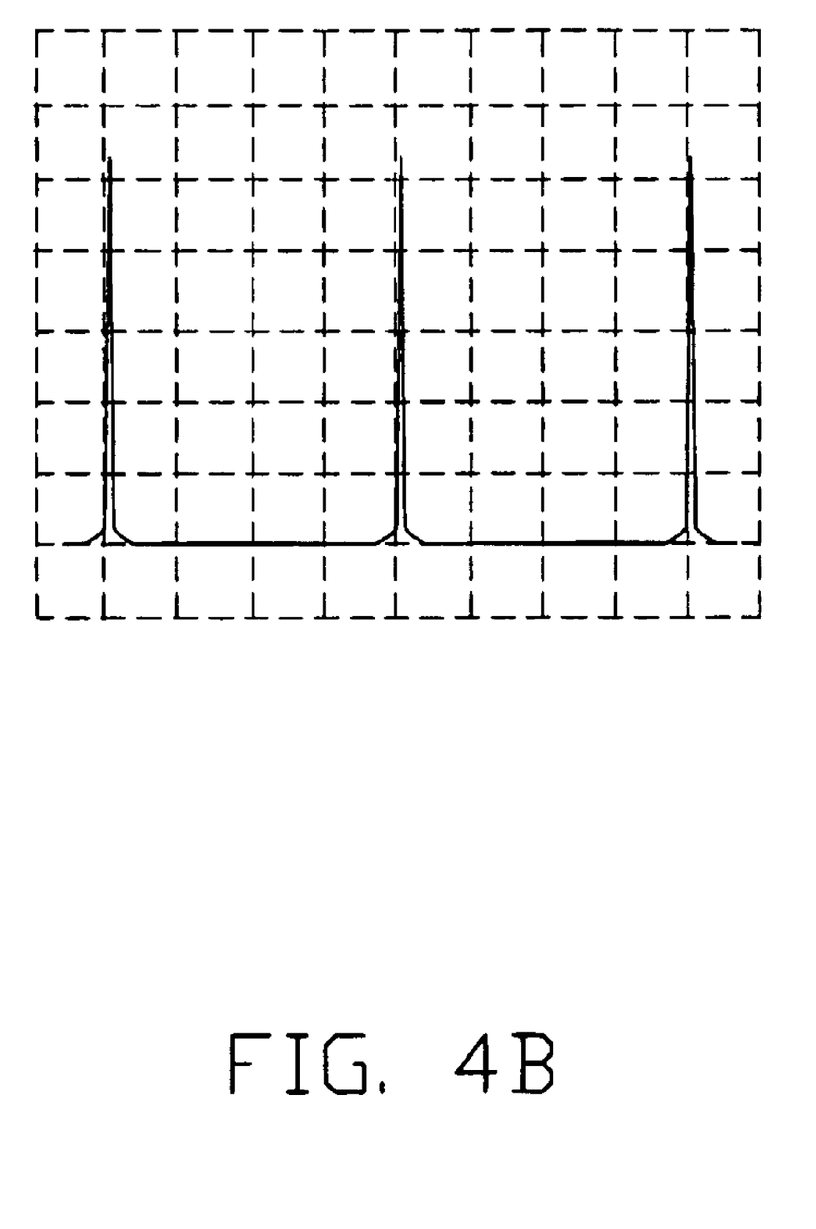

Referring to FIGS. 1 and 4, in a third method for inspecting the half-finished color filter 200, the stage 10 is moved along a Y direction, and only the light source 60 is turned on. Under this condition, an image (referring to FIG. 4A) and a signal (referring to FIG. 4B) of the color filter 200 are displayed on the monitor and the oscilloscope 52, respectively. The peak signal on the oscilloscope indicates the position of the black matrix.

Figure 5A:
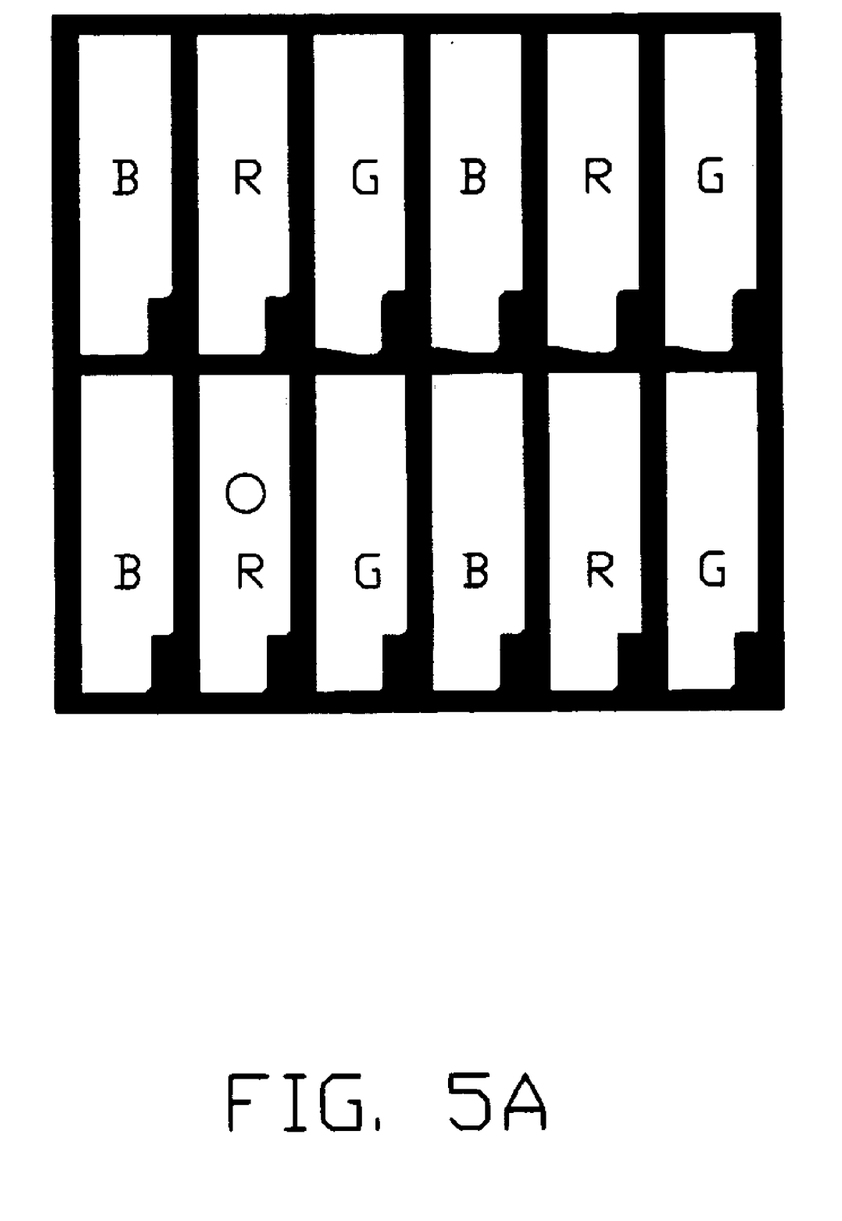
FIGS. 5A and 5B are an image and a graph displayed by the inspecting system of FIG. 1 in a fourth inspecting method.
Figure 5B:
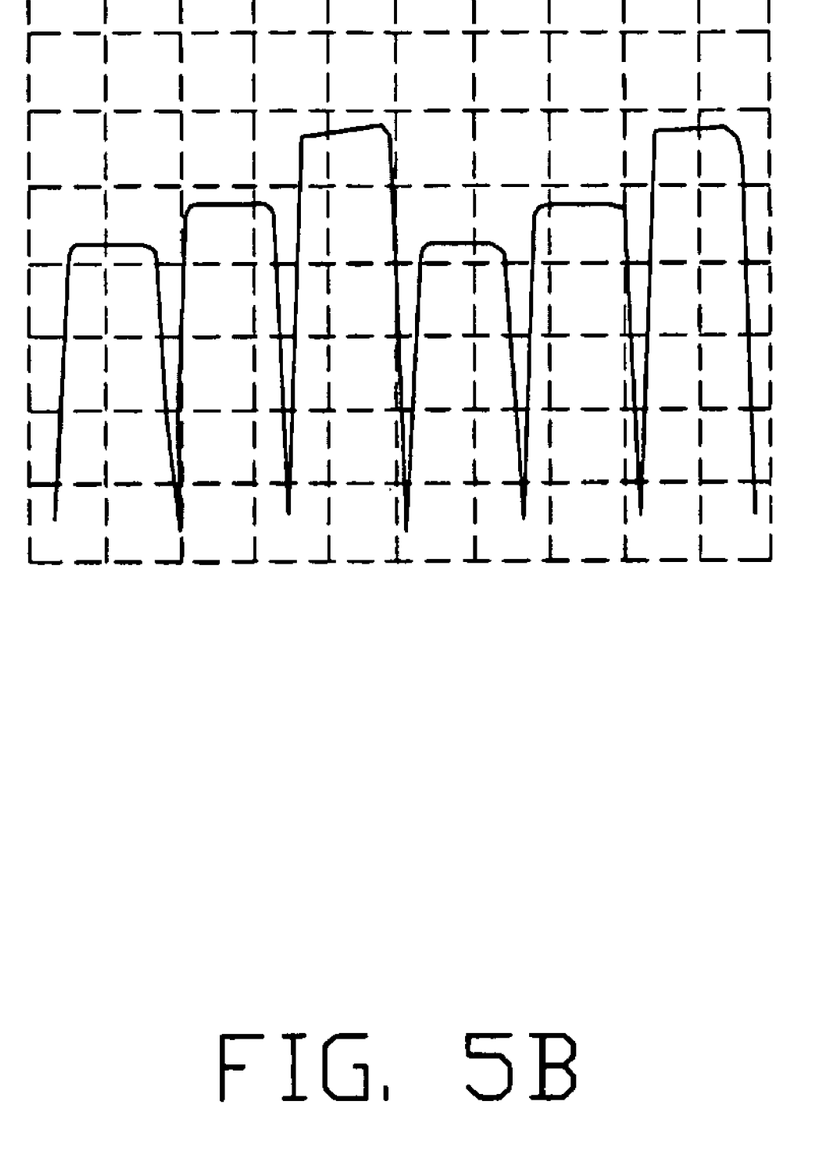

Referring to FIGS. 1 and 5, in a fourth method for inspecting the finished color filter 200, the stage 10 is moved along an X direction, and only the white light source 20 is turned on. Under this condition, the light source 20 emits the illuminating light 22. The lens 24 focuses the illuminating light 22 on a spot of the finished color filter 200. The spot size can be adjusted, using the lens 24. In this method, the spot size is smaller than that of the colored portion of the color filter 200, in the X direction. The CCD camera 40 can photograph a portion of the finished color filter 200, and a photographed image of the portion is displayed on the monitor of the image processing and displaying device 42 (referring to FIG. 5A). Because the image is enlarged, an inspection person can conveniently consider the quality of the black matrix and the colored portions of the finished color filter 200.

At the same time, the R, G, B lights of the illuminating light 22 are able to transmit the R, G, B colored portions of the color filter 200. The R, G, B lights pass through the beam splitter 38 and incidence/impinge upon the beam splitter 34. The beam splitter 34 reflects the R, G, B lights to the beam splitter 36. The R, G, B lights then pass through the beam splitter 36 and incidence upon the photo diode 50. The photo diode 50 receives the light signal of the R, G, B lights and generates a corresponding electronic signal. The oscilloscope 52 displays the electronic signal and aids the inspector's evaluation of the quality of the black matrix of the color filter 200 (referring to FIG. 5B). The signal on the oscilloscope indicates a relative intensity and an intensity distribution of the R, G, B colored portions for the same color at a different pixel.

Figure 6A:
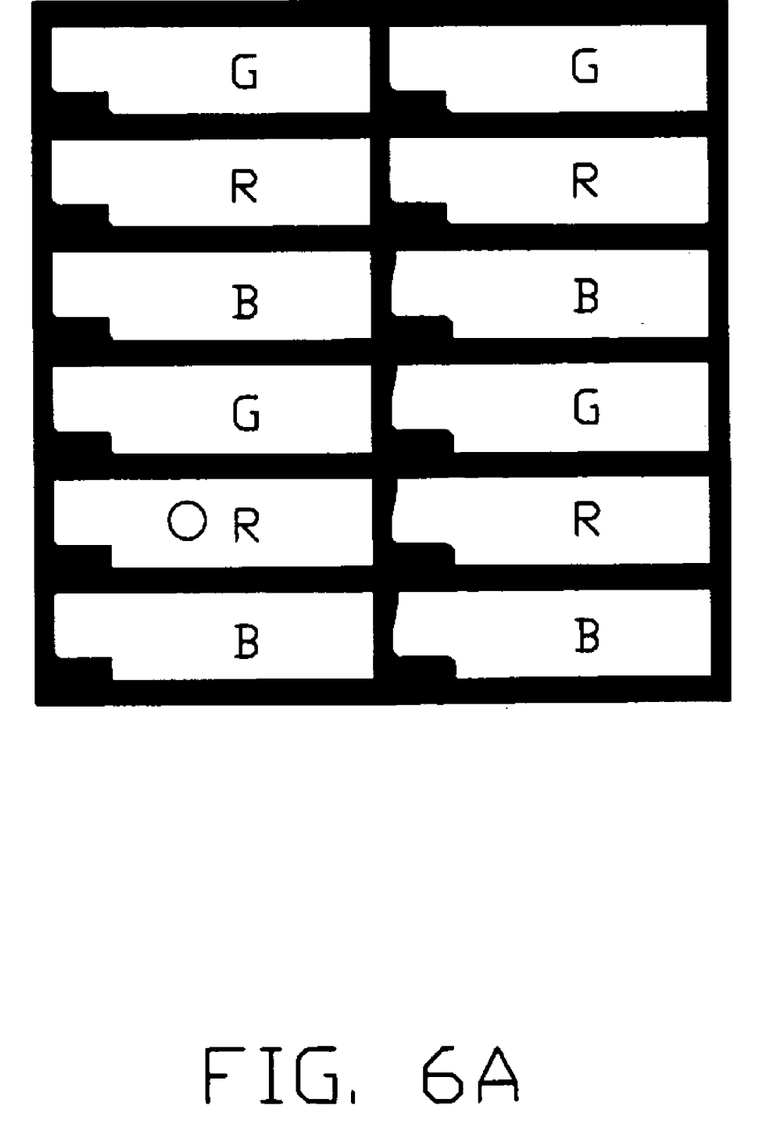
FIGS. 6A and 6B are an image and a graph displayed by the inspecting system of FIG. 1 in a fifth inspecting method.
Figure 6B:
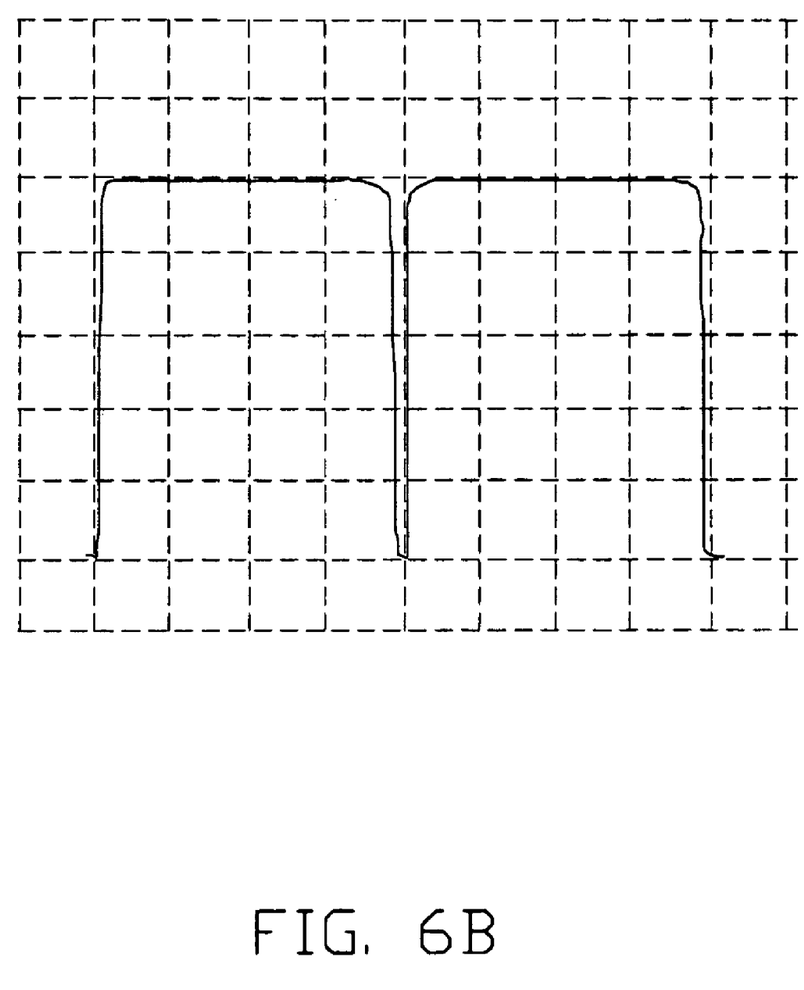

Referring to FIGS. 1 and 6, in a fifth method for inspecting the finished color filter 200, the stage 10 is driven along a Y direction, and only the light source 60 is turned on. Under this condition, an image (referring to FIG. 6A) and a signal (referring to FIG. 6B) of the finished color filter 200 are displayed on the monitor and the oscilloscope 52, respectively. The signal on the oscilloscope 52 indicates color intensity and uniformity of one colored portion, such as the red color.

Figure 7:
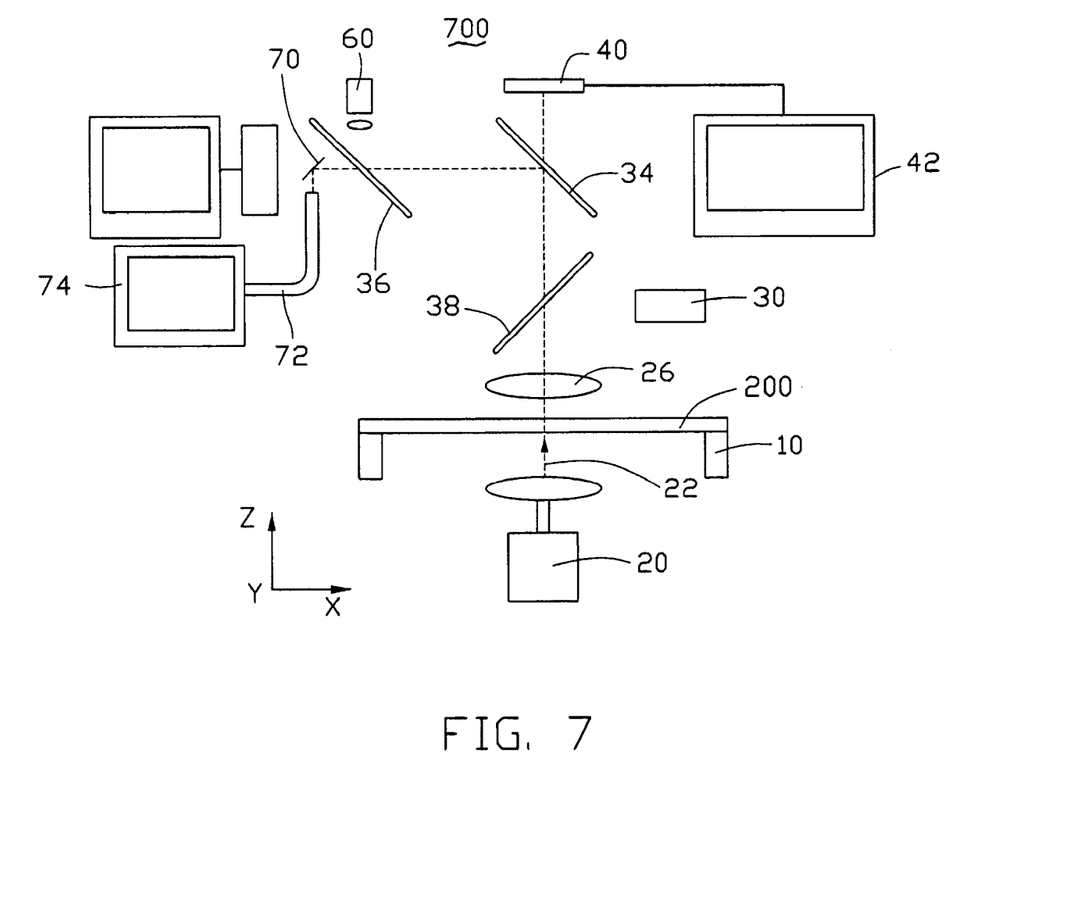
FIG. 7 is a schematic, plan view of an inspecting system, in accordance with a second embodiment.

Referring to FIG. 7, an inspecting system 700 for inspecting color filters, in accordance with a second embodiment, is shown. The inspecting system 700 is similar to the inspecting system 100 of the first embodiment and further includes an optical switch 70, an optical fiber 72, and a signal processing and displaying device 74. The optical switch 70 can be, e.g., a reflector and can move to a position to reflect the light 22 passing through the beam splitter 38, 34, 36 to the optical fiber 72. The optical fiber 72 can receive the reflected light 22 and guide it to the signal processing and displaying device 74. In the second embodiment, the signal processing and displaying device 74 is an optical spectrum analyzer.

Figure 8A:
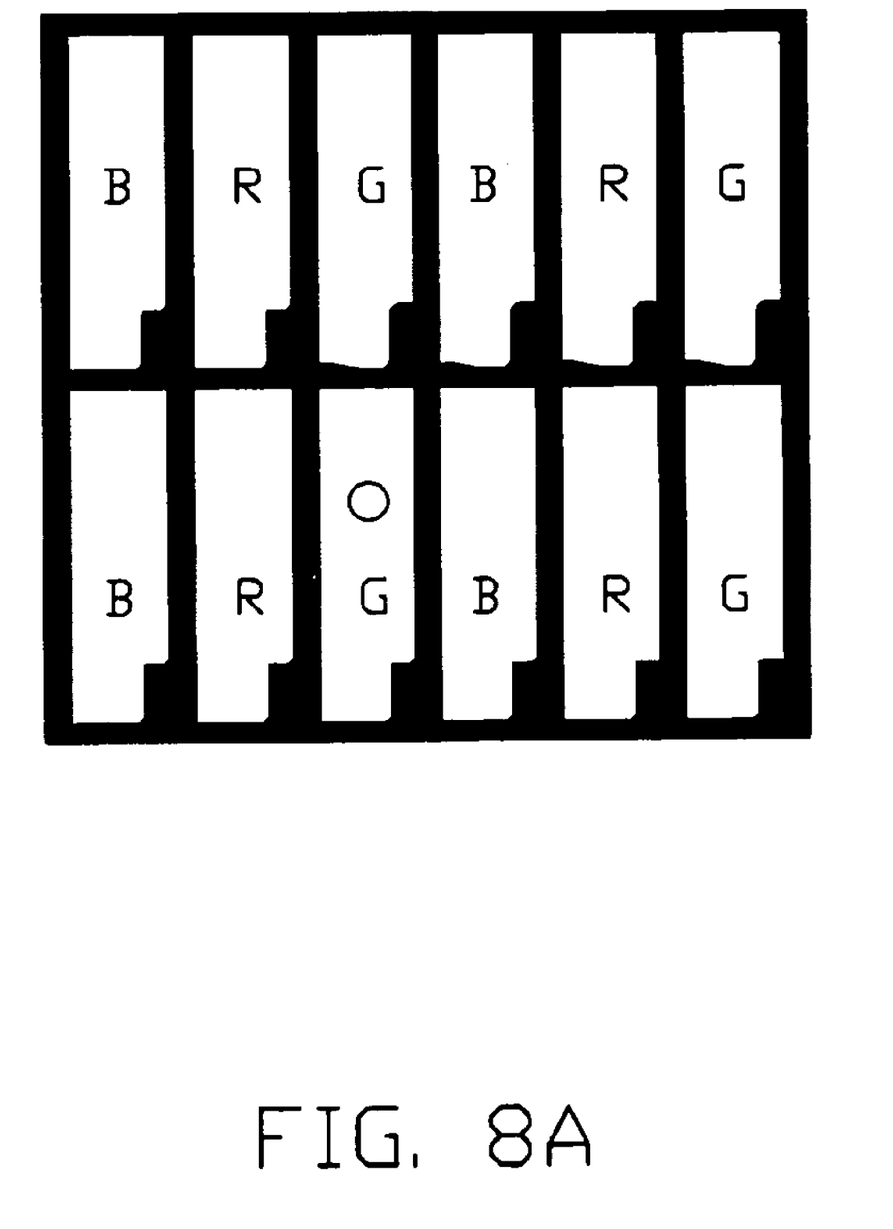
FIGS. 8A and 8B are an image and a graph displayed by the inspecting system of FIG. 7.
Figure 8B:
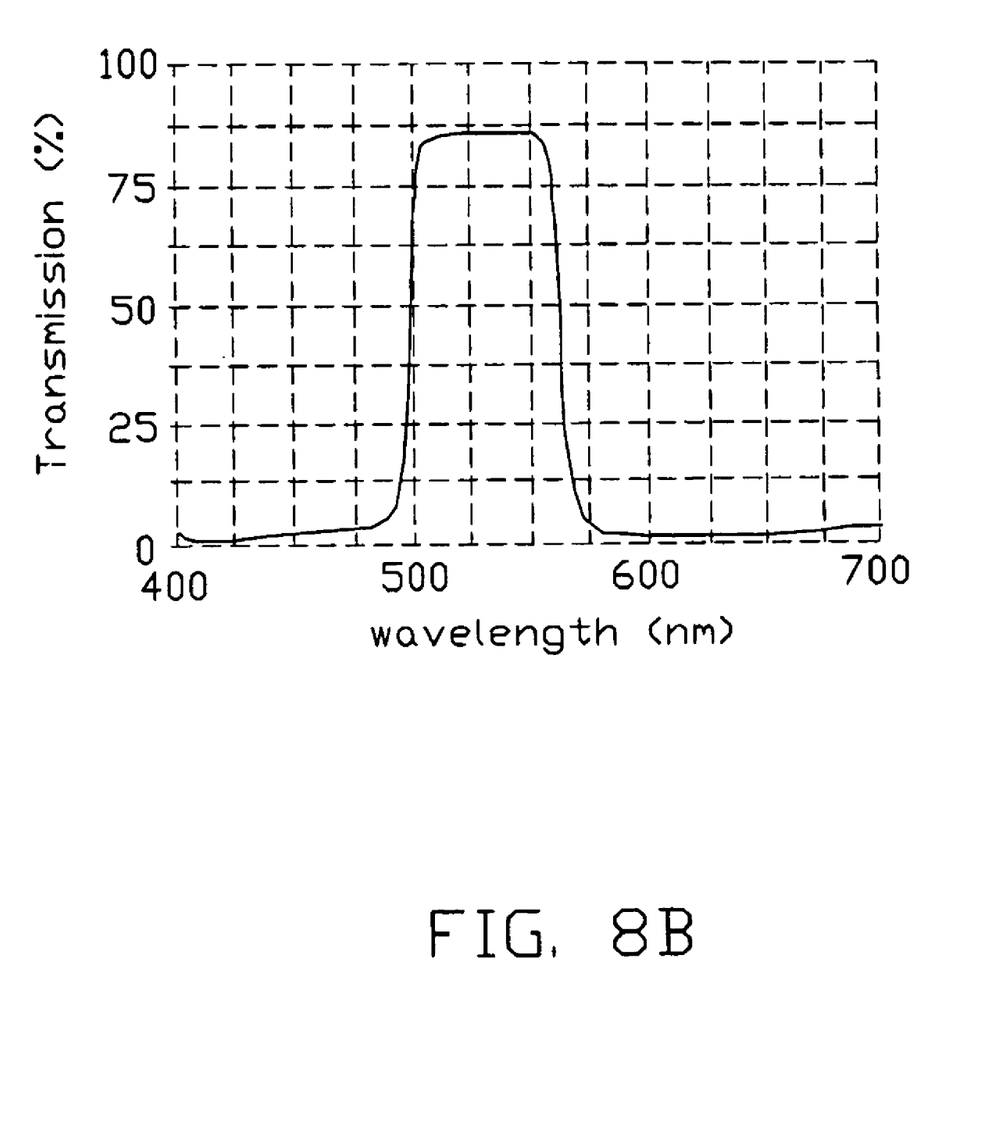

Referring to FIGS. 7 and 8, in a method for inspecting the finished color filter 200, the stage 10 is kept immobile, only the light source 20 is turned on, and the optical switch 70 is moved to the selected position in order to reflect the light 22 to the optical fiber 72. Under this condition, an image (referring to FIG. 8a) and a signal (referring to FIG. 8b) of the color filter 200 are displayed on the monitor and the optical spectrum analyzer 74, respectively. The signal on the optical spectrum analyzer 74 indicates the relation of transmission percentage and the wavelength of a light, such as green light. The other use methods of the inspecting system 700 are similar to the inspecting system 100 of the first embodiment.

Figure 9:
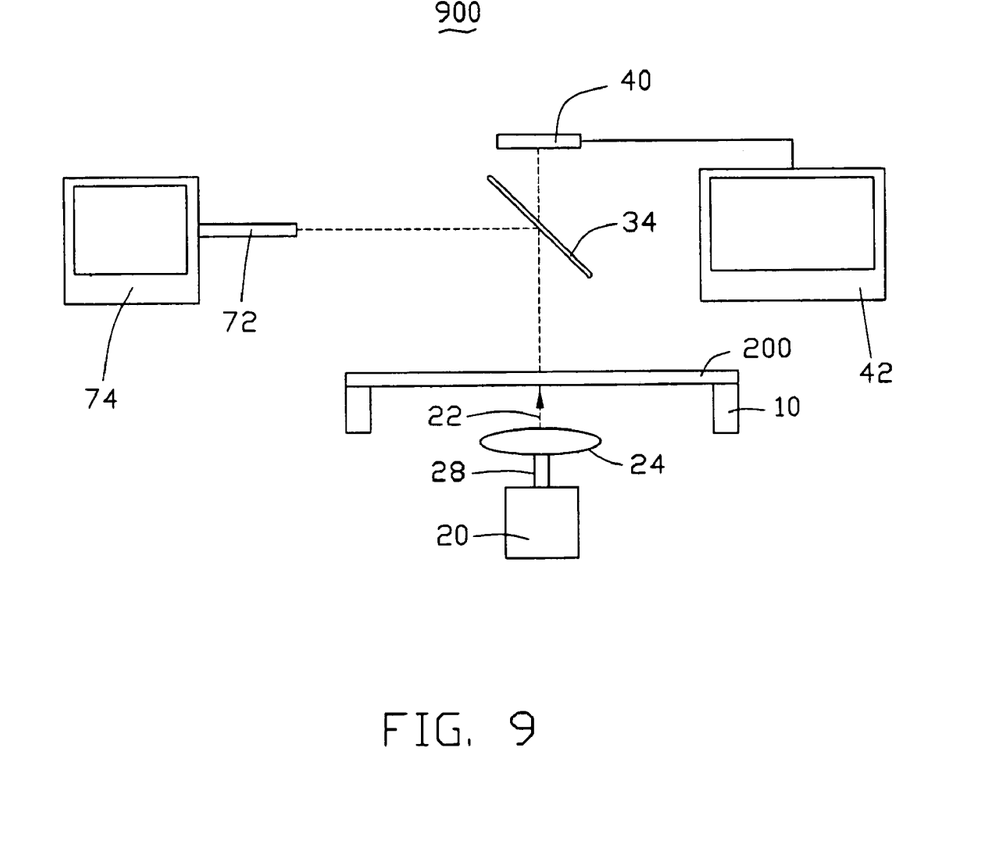
FIG. 9 is a schematic, plan view of an inspecting system, in accordance with a third embodiment.

Referring to FIG. 9, an inspecting system 900 for inspecting the finished color filter 200, in accordance with a third embodiment, is shown. The inspecting system 900 includes a stage 10, a CCD (charge coupled device) camera 40, a white light source 20, and a signal processing and displaying device 74. The CCD camera 40 connects with an image processing and displaying device 42. A beam splitter 34 is arranged between the CCD camera 40 and the finished color filter 200 located on the stage 10.

Specifically, the light source 20 is used for emitting an illuminating light 22 to illuminate the finished color filter 200 from a backside thereof. In order to focus the light 22 on a desirable spot of the color filter 200, a lens 24 can be mounted between the light source 20 and the color filter 200. Further, an optical fiber 28 can opportunely be used for guiding the light 22 emitted from the light source 20 to the lens 24, so that a variety of mounting places for the light source 20 may be suitable. In the third embodiment, the signal processing and displaying device 74 is an optical spectrum analyzer and is adapted/structured and arranged/positioned for receiving the white light 22 transmitted from the color filter. In addition, an optical fiber 72 can be used for guiding the light 22 to the optical spectrum analyzer 74, so that a mounting place of the optical spectrum analyzer 74 can likewise potentially be varied. The inspecting system 900 can be used for evaluating/examining the finished color filter 200, and its use method is similar to the inspecting system 700 described above.

It is to be understood that the above-described embodiment is intended to illustrate rather than limit the invention. Variations may be made to the embodiment without departing from the spirit of the invention as claimed. The above-described embodiments are intended to illustrate the scope of the invention and not restrict the scope of the invention.

What is claimed is:

1. An inspecting system for inspecting a color filter, comprising:
   a stage configured for supporting the color filter;
   a white light source structured and arranged for emitting a white light to illuminate the color filter from a first side of the color filter;
   a CCD camera configured for photographing the color filter from a second side of the color filter, the second side thereof being opposite to the first side thereof;
   an image processing and displaying device operatively connected with the CCD camera;
   a laser diode assembly configured for emitting a laser light;
   at least one beam splitter arranged in a path of the laser light and used for transmitting the laser light to the color filter;
   a photo diode configured for receiving the laser light via the at least one beam splitter and for thereby generating an electronic signal; and
   a first signal processing and displaying device connected with the photo diode, the first signal processing and displaying device being adapted for displaying the electronic signal generated by the photo diode.

2. The inspecting system as claimed in claim 1, wherein a first lens is mounted between the white light source and the color filter, the first lens being configured for focusing the white light on a desirable spot of the color filter.

3. The inspecting system as claimed in claim 2, wherein the white light source further comprises an optical fiber adapted for guiding the white light to the first lens.

4. The inspecting system as claimed in claim 1, further comprising a light emitting diode configured for emitting an illuminating light, and a beam splitter structured and arranged for reflecting the illuminating light in a manner so as to illuminate the color filter from the second side.

5. The inspecting system as claimed in claim 4, further comprising a second lens configured for focusing the illuminating light on a desirable spot of the color filter.

6. The inspecting system as claimed in claim 1, wherein the laser diode assembly further comprises a third lens positioned and adapted for focusing the laser light.

7. The inspecting system as claimed in claim 1, wherein the first signal processing and displaying device is an oscilloscope.

8. The inspecting system as claimed in claim 1, further comprising a second signal processing and displaying device adapted for receiving the white light transmitted from the color filter.

9. The inspecting system as claimed in claim 8, wherein the second signal processing and displaying device is an optical spectrum analyzer.

10. The inspecting system as claimed in claim 9, further comprising an optical switch and an optical fiber, wherein the optical switch is capable of moving to a position to reflect the white light transmitted from the color filter to the optical fiber, and the optical fiber is configured for receiving the white light and guiding it to the optical spectrum analyzer.

11. An inspecting system for inspecting a color filter, comprising:
    a stage adapted for supporting the color filter;
    a white light source structured and arranged for emitting a white light to illuminate the color filter from a first side of the color filter;
    a CCD camera configured for photographing the color filter from a second side of the color filter, the second side thereof being opposite to the first side thereof, the CCD camera connecting with an image processing and displaying device;
    a first beam splitter arranged in a path of the white light and adapted for reflecting the white light; and
    an optical spectrum analyzer positioned and adapted for receiving the white light reflected from the first beam splitter.

12. The inspecting system as claimed in claim 11, further comprising:
   a laser diode assembly adapted for emitting a laser light;
   a second beam splitter arranged in a path of the laser light and configured for transmitting the laser light to the color filter through the first beam splitter;
   a photo diode arranged for receiving the laser light reflected by the color filter and adapted for generating an electronic signal;
   an oscilloscope connected with the photo diode, the oscilloscope being configured for displaying the electronic signal generated by the photo diode.

13. The inspecting system as claimed in claim 12, further comprising an optical switch, the optical switch being structured and arranged for receiving the laser light reflected by the color filter and reflecting such laser light to the photo diode.

14. The inspecting system as claimed in claim 12, wherein the laser diode assembly further comprises a third lens adapted for focusing the laser light.

15. The inspecting system as claimed in claim 11, wherein the optical spectrum analyzer is connected with an optical fiber, the optical fiber being configured for receiving the white light and guiding it to the optical spectrum analyzer.

16. The inspecting system as claimed in claim 11, wherein a first lens is mounted between the white light source and the color filter, the first lens being adapted for focusing the white light on a desirable spot of the color filter.

17. The inspecting system as claimed in claim 16, wherein the white light source further comprises an optical fiber positioned and structured for guiding the white light to the first lens.

18. The inspecting system as claimed in claim 11, further comprising a light emitting diode adapted for emitting an illuminating light, and a beam splitter positioned and designed for reflecting the illuminating light so as to illuminate the color filter from the second side thereof.

19. The inspecting system as claimed in claim 18, further comprising a second lens configured for focusing the illuminating light on a desirable spot of the color filter.

* * * * *